(12) United States Patent
Day et al.

(10) Patent No.: US 7,169,116 B2
(45) Date of Patent: Jan. 30, 2007

(54) ACTUATION SYSTEM FOR A BODILY FLUID EXTRACTION DEVICE AND ASSOCIATED METHODS

(75) Inventors: Richard Day, Nairn (GB); Manuel Alvarez-Icaza, Inverness (GB); Simon Palmer, Inverness (GB)

(73) Assignee: LifeScan, Inc., Milpitas, CA (US)

( * ) Notice: Subject to any disclaimer, the term of this patent is extended or adjusted under 35 U.S.C. 154(b) by 362 days.

(21) Appl. No.: 10/837,479

(22) Filed: Apr. 29, 2004

(65) Prior Publication Data

US 2005/0245843 A1 Nov. 3, 2005

(51) Int. Cl.
*A61B 5/00* (2006.01)

(52) U.S. Cl. .............. 600/583; 600/573; 600/576; 600/584

(58) Field of Classification Search .......... 600/573, 600/576, 583, 584; 606/181, 182
See application file for complete search history.

(56) References Cited

U.S. PATENT DOCUMENTS

| 5,871,494 | A | 2/1999 | Simons et al. |
| 6,135,969 | A * | 10/2000 | Hale et al. ............... 600/595 |
| 6,319,210 | B1 | 11/2001 | Douglas et al. |
| 6,364,889 | B1 | 4/2002 | Kheiri et al. |
| 6,530,892 | B1 | 3/2003 | Kelly |
| 2001/0039419 | A1 * | 11/2001 | Francischelli et al. ........ 606/42 |
| 2003/0018300 | A1 | 1/2003 | Duchon et al. |
| 2005/0209625 | A1 * | 9/2005 | Chan ........................ 606/181 |

* cited by examiner

Primary Examiner—Charles Marmo
Assistant Examiner—Anuradha Roy
(74) Attorney, Agent, or Firm—Mayumi Maeda; LifeScan, Inc.

(57) ABSTRACT

An actuation system for a bodily fluid extraction device includes a detector cap, at least one vibration sensor connected to the detector cap, and at least one signal processing unit in communication with the vibration sensor. In addition, the signal processing unit is configured to receive an output signal from the vibration sensor, analyze the received output signal, and to send an actuation signal to the bodily fluid extraction device based on the analysis of the received output signal.

3 Claims, 5 Drawing Sheets

ACTUATION SYSTEM FOR A BODILY FLUID EXTRACTION DEVICE AND ASSOCIATED METHODS

BACKGROUND OF THE INVENTION

1. Field of the Invention

This application relates, in general, to medical devices and, in particular, to medical devices for the extraction of bodily fluid and their associated methods.

2. Background to the Invention

A variety of medical conditions, such as diabetes, call for the monitoring of an analyte concentration (e.g., glucose concentration) in a blood, interstitial fluid or other bodily fluid sample. Typically, such monitoring requires the extraction of a bodily fluid sample from a target site (e.g., a dermal tissue target site on a user's finger). The extraction (also referred to as "expression") of a bodily fluid sample from the target site generally involves lancing the dermal tissue target site and applying pressure in the vicinity of the lanced site to express the sample.

It is known to employ various bodily fluid extraction devices (e.g., spring-loaded lancing devices) to aid in the expression of a bodily fluid sample. Such bodily fluid extraction devices typically require a user to prime the device, urge the device against a target site, and then press a button or other switch to manually activate the device such that a dermal tissue penetration member (e.g., a lancet) within the device is launched towards the target site. The dermal tissue penetration member then penetrates (e.g., lances) the target site, thereby creating an opening for the expression of a bodily fluid sample.

Extraction of a bodily fluid sample using conventional bodily fluid extraction devices can induce pain and/or discomfort in a user. A portion of such pain and/or discomfort is due to the physical penetration of the target site by the dermal tissue penetration member. However, a significant portion of such pain and/or discomfort can also be mental in nature due to the user's apprehensive anticipation of target site penetration and any disconcerting noise related to manually activating the device. This apprehension typically occurs as the user is urging the bodily fluid extraction device toward the target site and is consciously deciding whether or not to launch the dermal penetration member. In addition, the apprehension can lead to increased pain and/or discomfort due to a user physically tensing the target site in anticipation of penetration.

Pain and/or discomfort to a user can also occur when an attempt to extract a bodily fluid sample is unsuccessful and a user must make another attempt to extract a bodily fluid sample. Unsuccessful attempts to extract a bodily fluid sample can occur, for example, when a bodily fluid extraction device is not in the proper orientation while urged against a target site or has not been urged against the site with the proper pressure.

Still needed in the field, therefore, are a medical device and associated methods that decrease pain and/or discomfort associated with extracting a bodily fluid sampled due to either a user's apprehensive anticipation of target site penetration and/or unsuccessful attempts to extract a bodily fluid sample.

SUMMARY OF THE INVENTION

Medical devices and methods according to embodiments of the present invention serve to decrease pain and/or discomfort associated with extracting a bodily fluid sample due to a user's apprehensive anticipation of target site penetration. The medical devices and methods also serve to minimize unsuccessful attempts at extracting a bodily fluid sample. Medical devices according to embodiments of the present invention include both actuation systems for bodily fluid extraction devices and bodily fluid extraction devices that include an actuation system.

Embodiments of actuation systems for a bodily fluid extraction device according to the present invention include a detector cap, at least one vibration sensor connected to the detector cap, and at least one signal processing unit in communication with the at least one vibration sensor. In addition, the signal processing unit is configured to receive an output signal from the at least one vibration sensor, analyze the received output signal, and to send an actuation signal to the bodily fluid extraction device based on the analysis of the received output signal.

Actuation systems according to embodiments of the present invention decrease user pain and/or discomfort associated with apprehensive anticipation of target site penetration by eliminating the need for a user to manually actuate the bodily fluid extraction device. Instead of manual actuation by a user, the signal processing unit automatically sends an actuation signal to the bodily fluid device based on an analysis of the output signals received from the vibration sensor(s). In addition, analysis of the received signal can serve to indicate when the bodily fluid extraction device has been properly urged against the target site, thus minimizing unsuccessful bodily fluid extraction attempts.

Embodiments of bodily fluid extraction devices according to the present invention include a housing, a lancing mechanism that is moveable with respect to the housing, a lancet attached to the lancing mechanism, an automatic firing mechanism and an actuation system. Furthermore, the actuation system includes a detector cap, at least one vibration sensor connected to the detector cap, and at least one signal processing unit in communication with the at least one sensor.

The signal processing unit of the bodily fluid extraction device is configured to receive an output signal from the at least one vibration sensor, to analyze the received output signal, and to send an actuation signal to the automatic firing mechanism based on the analysis of the received signal.

BRIEF DESCRIPTION OF DRAWINGS

A better understanding of the features and advantages of the present invention will be obtained by reference to the following detailed description that sets forth illustrative embodiments, in which the principles of the invention are utilized, and the accompanying drawings (wherein like numerals represent like elements), of which.

DETAILED DESCRIPTION OF THE INVENTION

Figure 1A:
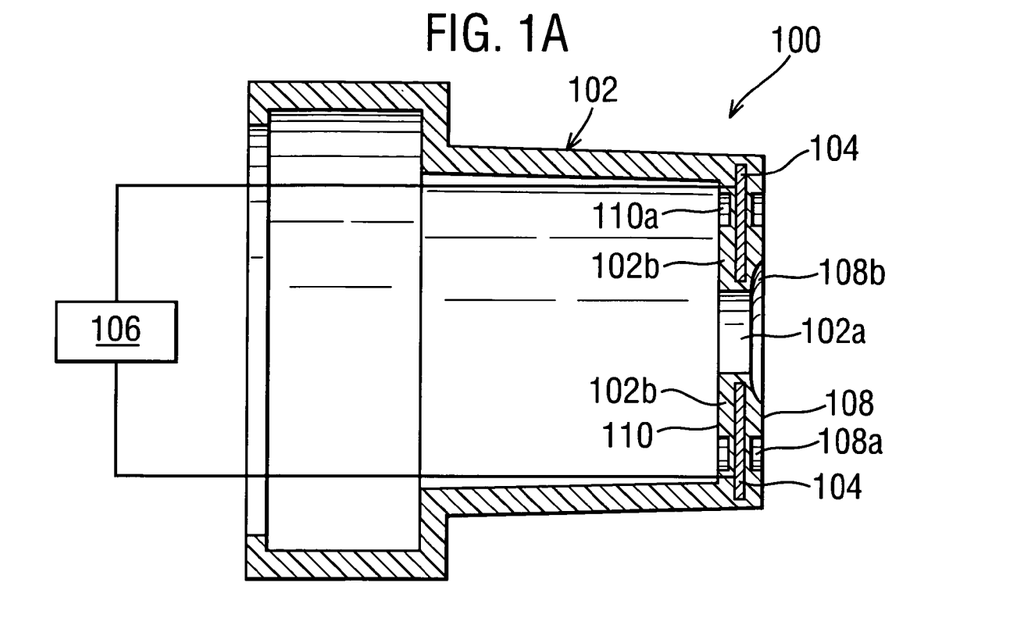
FIG. 1A is a simplified, cross-sectional and schematic depiction (not to scale) of an actuation system according to an exemplary embodiment of the present invention.
Figure 1B:
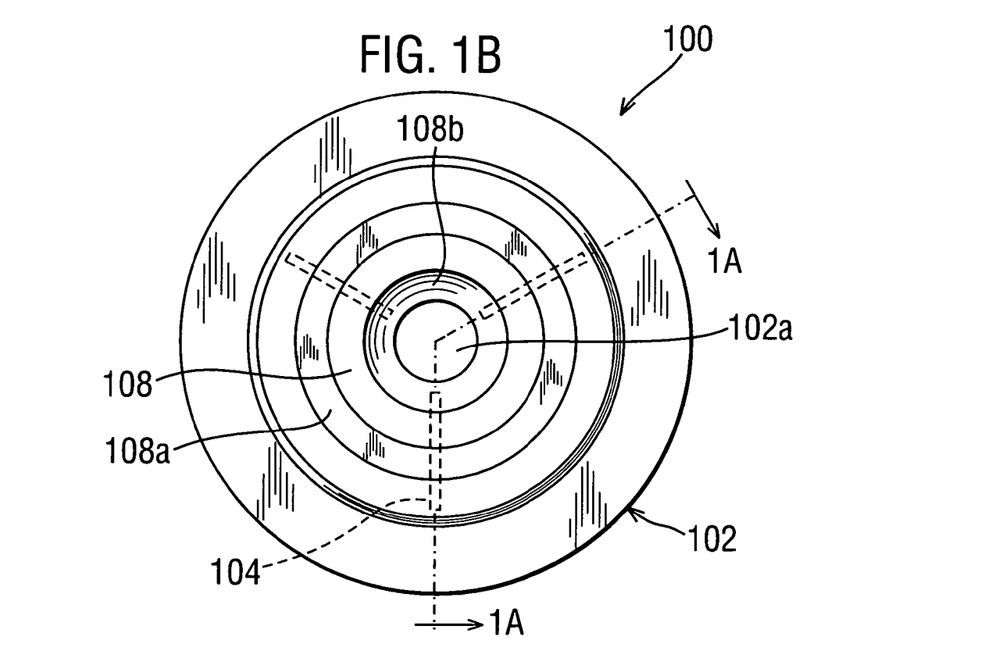
FIG. 1B is a simplified bottom view (i.e. a view toward the distal end of the detector cap) of the actuation system of FIG. 1A.

FIGS. 1A and 1B are simplified perspective/schematic and bottom view depictions, respectively, of an actuation system 100 for a bodily fluid extraction device according to an exemplary embodiment of the present invention. Referring to FIGS. 1A and 1B, actuation system 100 includes a detector cap 102, at least one vibration sensor(s) 104 connected to detector cap 102 and a signal processing unit (SPU) 106 in communication with vibration sensor(s) 104.

Detector cap 102 includes a distal surface 108 and a proximal surface 110. Furthermore, detector cap 102 includes an aperture 102a and a deflectable portion 102b. In the embodiment of FIGS. 1A and 1B, vibration sensors 104 are embedded in the detector cap beneath distal surface 108. However, vibration sensor(s) 104 can be connected to detector cap 102 using any suitable technique including, for example, surface mounting. Furthermore, signal processing unit 106 is configured to receive output signals from each of the vibration sensors 104, to analyze the received output signals, and to send an actuation signal to the bodily fluid extraction device based on the analysis of the received output signal.

Distal surface 108 and proximal surface 110 include recesses 108a and 110a, respectively. In addition, distal surface 108 also includes an indented portion 108b. When force is applied to distal surface 108 (e.g., a force resulting from the urging of detector cap 102 against a target site), deflectable portion 102b of detector cap 102 is configured to flex inward (from right to left in the view of FIG. 1A). In so doing, vibration sensor(s) 104 is placed under a bending mechanical stress. As explained in further detail below, in the circumstance that vibration sensor(s) 104 is a piezo-vibration sensor, vibration sensor(s) 104 will, for example, produce a voltage signal in response to vibrations (for example, vibrations in the range of 10 microns to 100 microns in amplitude) caused by the pulsing of blood through the target site.

In actuation system 100, detector cap 102 is shaped to fit securely on the housing of a bodily fluid extraction device. However, detector caps of any suitable shape can be employed in actuation systems of the present invention. Detector cap 102 can be formed, for example, from a resiliently deformable material, including, but not limited to, an elastomeric material, a polymeric material, a polyurethane material, a latex material, a silicone material and any combination thereof. Such resiliently deformable materials can, for example, deform to assume the contour of a target site (e.g., a dermal tissue target site on a user's finger) against which distal surface 108 of the detector cap is urged during use. Alternatively, detector cap 102 can be formed, for example, from rigid materials such as rigid plastic materials or rigid metallic materials.

Vibration sensors 104 can be any suitable vibration sensors known to one skilled in the art including, for example, piezo-vibration sensors (e.g., bimorph 32 piezo-vibration sensors available from RS Components, Northants, UK) and accelerometer sensors. In the embodiment of FIGS. 1A and 1B, vibration sensors 104 are embedded beneath the distal surface 108 of detector cap 104. However, the vibration sensors can, alternatively, be partially embedded or otherwise attached to detector cap 102. Although, for the purpose of explanation only, three vibration sensors are shown in the embodiment of FIGS. 1A and 1B, actuation system according to embodiments of the present invention can have any suitable number of vibration sensors. Vibration sensors can be disposed on/in the detector cap in any suitable arrangement. For a more accurate detection of vibration and determination of the proper orientation of the detector cap against a target site, it is preferred that vibration sensors 104 are substantially equally spaced about the circumference of detector cap 104, as shown in FIGS. 1A and 1B.

One skilled in the art will recognize that vibration sensors 104 serve to convert mechanical vibratory energy into electrical energy. For example, a piezo-vibration sensor can produce an electrical output that is proportional to the magnitude of a mechanical stress induced on the piezo-vibration sensor. Thus, when a piezo-vibration sensor experiences a vibration induced mechanical stress, the piezo-vibration sensor produces an output signal (e.g., an output voltage signal) that is proportional to the mechanical stress.

Blood pulsing through a target site induces vibrations that can be sensed by vibration sensors 104 as detector cap 102 is urged against the target site. These vibrations result in each of vibration sensors 104 producing an output signal (such as an output voltage signal). A typical output voltage signal can be, for example, in the range 4V peak to peak.

The output signals from each of the vibration sensors 104 are communicated to signal processing unit 106, wherein they are received and analysed. Signal processor unit 106 can be any signal processing unit or combination of signal processing units known to those of skill in the art. For example, signal-processing unit 106 can be a logic signal-processing unit, an Application Specific Integrated Circuit (ASIC) or a programmable micro-processor.

When detector cap 102 is urged against a target site prior to the extraction of a bodily fluid sample therefrom, signal processing unit 106 can be employed to determine when detector cap is in an optimal orientation and position for bodily fluid extraction via analysis of the received output signals from vibration sensors 104. For example, the optimal orientation and position may correspond to output signals from each of the vibration sensors being within a predetermined range and matched within a predetermined tolerance to the output signals of the other vibration sensors. In the circumstance that the actuation system includes three identical vibration sensors (each connected to the detector cap in the same manner), the signal processing unit would receive output signals from each of the three vibration sensors and, for example, compare the output signals to one another and send an actuation signal only when the three output signals are in agreement within an acceptable error range. In this event, it is postulated without being bound, that the three output signals being in agreement indicates that each vibration sensor is experiencing the same vibration and that, therefore, the detector cap is squarely positioned against the target site.

Once apprised of the present disclosure, one skilled in the art will recognize that, in general terms, the signal processing unit is analyzing the output signal(s) from the vibration sensor(s) for the presence of a characteristic output signal that indicates proper positioning of the detector cap against a target site. Subsequent to the detection of the presence of such a characteristic output signal by the signal processing unit, the signal processing unit sends an actuation signal to the bodily fluid extraction device.

From the above explanation, one skilled in the art will recognize that the analysis of the output signals by the signal processing unit results in actuation of the bodily fluid extraction device only when the device has been properly urged against the target site. Conversely, improper urging (e.g., urging with an orientation that is not squarely against the target site) will not result in an activation signal being sent to the bodily fluid extraction device by the signal processing unit. Therefore, unsuccessful attempts at extracting a bodily fluid sample are minimized. Moreover, since a user is not required to manually actuate the bodily fluid extraction device, pain and/or discomfort associated with apprehension of penetration or the sound of manual actuation are eliminated.

Actuation system 100 of FIGS. 1A and 1B can include at least one optional pressure sensor (not shown in FIGS. 1A and 1B), each in communication with signal processing unit 106. Any suitable pressure sensor can be employed including, for example, a microswitch-based pressure sensor or pressure transducer (both of which are available from RS Components Ltd., Birchington Road, Corby, Northants, NN17 9RS, UK.)

Moreover, when an optional pressure sensor(s) is included in actuation system 100, signal processing unit 106 is further configured to receive a signal from each of the pressure sensors, to analyze the received signal from the pressure sensor, and to send an actuation signal to the bodily fluid extraction device based on the analysis of the received signal from the pressure sensor. Actuation systems according to embodiments of the present invention can have any suitable number of pressure sensors. Furthermore, such pressure sensors can, for example, be disposed on or in operative connection with the detector cap in any suitable arrangement. For a more accurate detection of pressure, it is preferred that such pressure sensors be disposed in substantially equally spaced apart relationship to one another.

Pressure sensors are optional in actuation systems according to the present invention. However, the inclusion of such sensors provides a means to monitor the force with which detector cap 102 is urged against a target site via analysis by the signal processing unit of the signals received from the pressure sensor(s). Therefore, use of pressure sensors provides additional information describing the relationship between detector cap 102 and the target site. For example, analysis of the signals from the pressure sensors can provide an indication of how firmly detector cap 102 is pressed against a target site, with the signal processing unit only sending an actuation signal when the analysis indicates that adequate pressure is present to insure successful expression of a bodily fluid sample.

Figure 2:
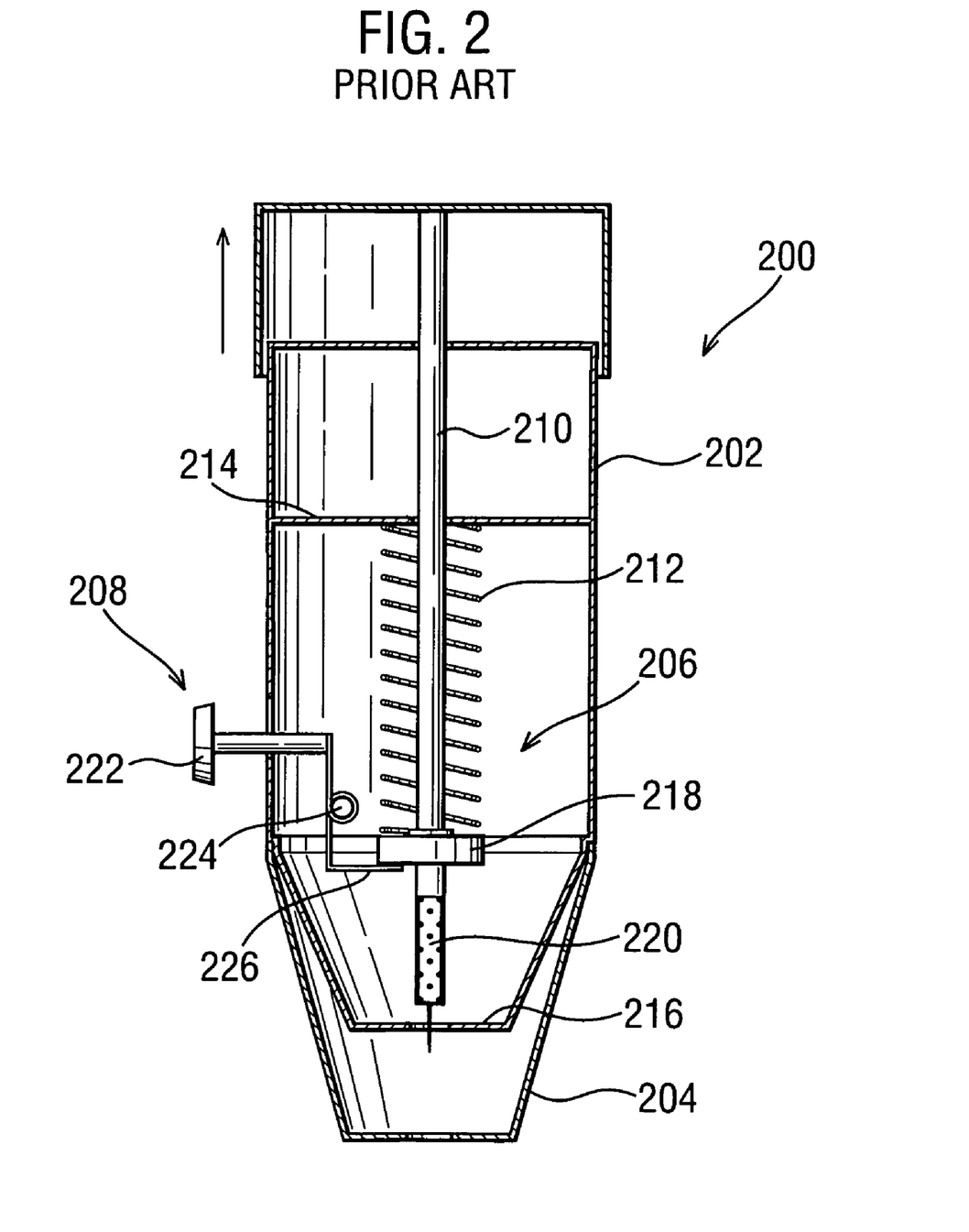
FIG. 2 is a simplified cross-sectional depiction (not to scale) of a conventional spring-loaded medical device for the extraction of bodily fluid (i.e., a lancing device) that can be combined with actuation systems according to exemplary embodiments of the present invention.

Actuation system 100 is configured for employment with a bodily fluid extraction device, such as a spring-loaded lancing device. FIG. 2 is a simplified cross-sectional depiction of a spring-loaded lancing device 200 with which actuation systems according to embodiments of the present invention can be employed. Spring-loaded lancing device 200 includes a housing 202, an end cap 204, a lancing mechanism 206 that is moveable with respect to the housing, and a firing mechanism 208.

Lancing mechanism 206 includes a primer 210, a spring 212, a backstop 214, an end stop 216, a lancet holder 218, and a lancet 220. Firing mechanism 208 includes a firing button 222, a pivot 224 and a catch 226.

The use of spring-loaded lancing device 200 to extract a bodily fluid sample (e.g., a blood sample) from a target site (such as a dermal tissue target site on a user's finger) would typically proceed as follows. After having installed lancet 220 in lancet holder 218, lancing mechanism 206 is primed by pulling primer 210 in the direction of the arrow in FIG. 2. Such priming causes (i) spring 212 to be compressed between backstop 214 and lancet holder 218 and (ii) catch 226 to latch with lancet holder 218, as depicted in FIG. 2. End cap 204 of spring-loaded lancing device 200 is then urged against the target site with sufficient pressure to insure expression of a bodily fluid sample following lancing of the target site. It is preferred that the end cap be symmetrically (squarely) urged against the target site since such a symmetrical orientation increases the likelihood of a successful extraction of a bodily fluid sample.

Thereafter, manual depression of firing button 222 by a user will cause firing mechanism 206 to pivot around pivot 224, retracting catch 226 and releasing lancet holder 218. The release of lancet holder 218 enables spring 212 to expand, launching lancet 220 towards the target site. Lancet holder 218 and end stop 216 prevent lancet 220 from traveling more than a predetermined distance.

As previously described, a user may have difficulty in symmetrically urging end cap 204 against a target site and in determining when sufficient pressure has been applied to the target site for expression of a bodily fluid sample. However, by employing actuation systems according to embodiments of the present invention with a bodily fluid extraction device (e.g., spring-loaded lancing device 200 of FIG. 2), symmetrical orientation and, optionally, sufficient pressure, can be sensed and employed to automatically actuate the bodily fluid extraction device.

Figure 3:
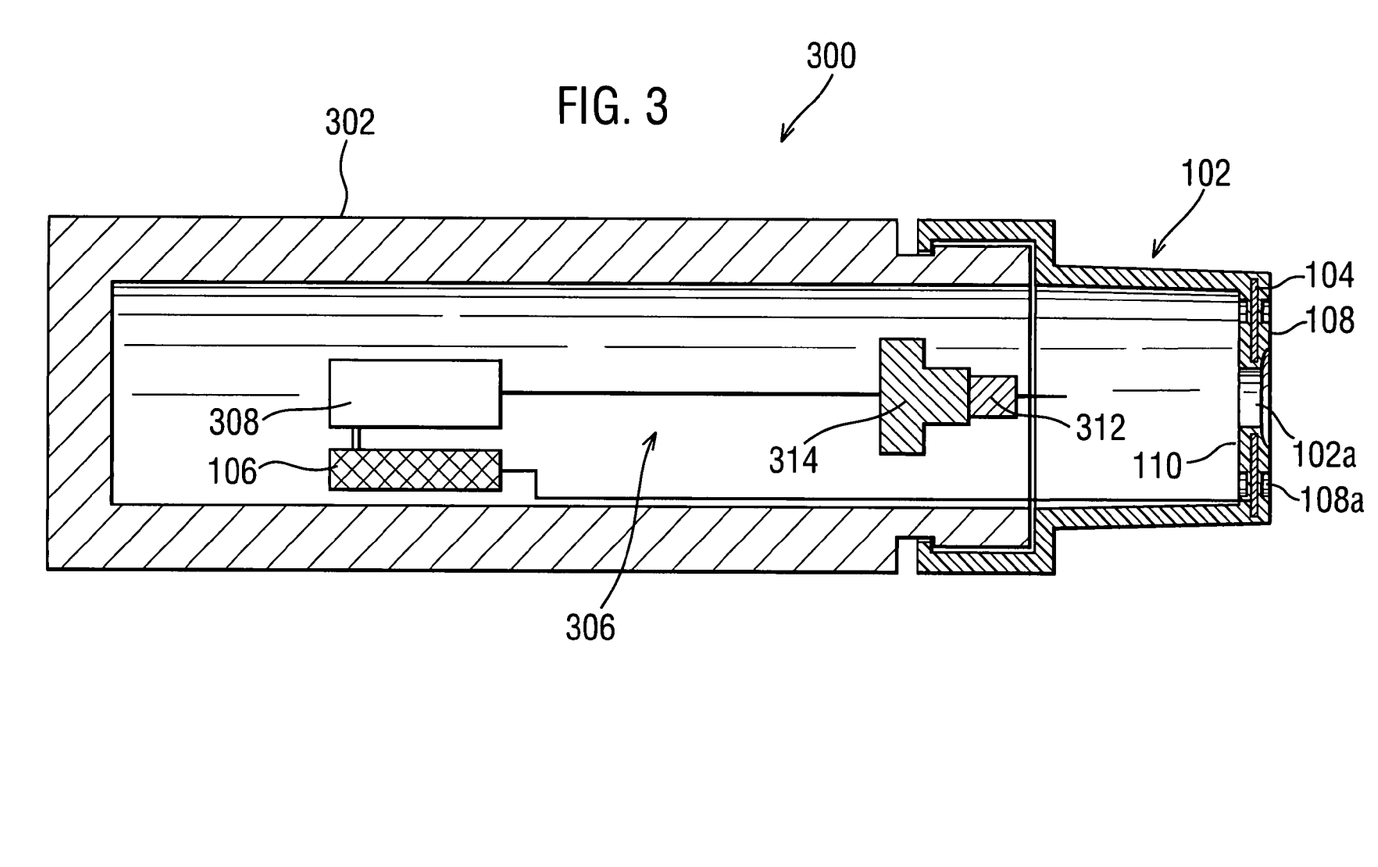
FIG. 3 is a simplified schematic cross-sectional view (not to scale) of a bodily fluid extraction device according to an exemplary embodiment of the present invention that includes the actuation system of FIG. 1.

FIG. 3 is a simplified schematic cross-sectional view of a bodily fluid extraction device 300 (e.g., a lancing device) according to an exemplary embodiment of the present invention that includes actuation system 100 of FIGS. 1A and 1B. Bodily fluid extraction device 300 also includes a housing 302, a lancing mechanism 306 (that is moveable with respect to housing 302), and an automatic firing mechanism 308. Lancing mechanism 306 includes a lancet 312 (e.g., an integrated lancet and test strip) and a lancet holder 314. Detector cap 102 includes an aperture 102a within which a target site bulge can be formed when detector cap 102 is urged against the target site.

Automatic firing mechanism 308 can be any suitable automated firing mechanism known to one skilled in the art including, but not limited to, the piezo-electric mechanism described in UK Patent Application No. 0323350.9 filed on 6 Oct. 2003). Other automated firing mechanisms could involve, for example, (i) electronically retracting a latch, to release a compressed spring, the expansion of which launches a lancet toward a target site or (ii) electromagnetic drivers.

As previously described, output signals from vibration sensors 104 are analyzed by signal processing unit 106 to determine when detector cap 102 is appropriately positioned while being urged against a target site. Conversely, the output signals from vibration sensors 104 can also be analyzed by the signal processing unit to detect improper positioning of detector cap 102 and preclude launching of lancet 312.

Once apprised of the present disclosure, one skilled in the art will recognize that embodiments of bodily fluid extraction devices according to the present invention can include a detector cap of various configurations including, for example, a single integrated detector cap that serves both as an end cap and a detector cap (as illustrated in FIG. 3).

Figure 4:
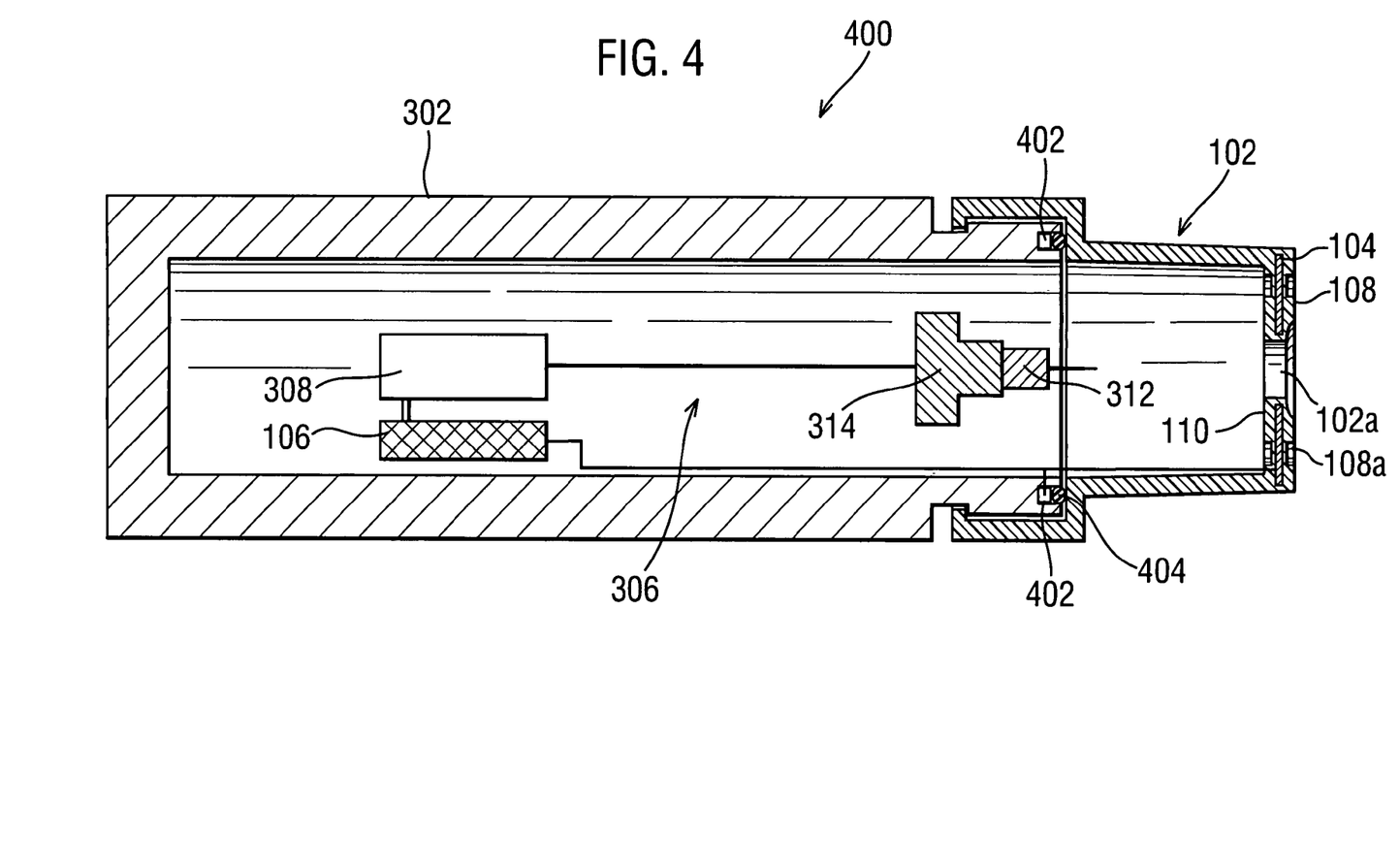
FIG. 4 is a simplified schematic cross-sectional view (not to scale) of the bodily fluid extraction device of FIG. 3 with the inclusion of optional pressure sensors in the actuation system.

FIG. 4 is a simplified schematic cross-sectional view of a bodily fluid extraction device 400 according to another exemplary embodiment of the present invention that is identical to device 300 of FIG. 3 but for (a) the inclusion of pressure sensors 402, (b) the inclusion of compressible o-ring 404 and (c) signal processing unit 106 being configured to receive a signal from pressure sensors 402, to analyze the received signals from pressure sensors 402, and to send an actuation signal to automatic firing mechanism 308 based on the analysis of the received signals from pressure sensors 402.

In the embodiment of FIG. 4, pressure sensors 402 are disposed between compressible o-ring 402 and housing 302 (i.e., pressure sensors 402 are indirectly connected to detector cap 102) such that the pressure with which detector cap 102 is urged against a target site can be sensed by pressure sensors 402. Although, for the purpose of explanation only, two pressure sensors 402 are shown in the embodiment of FIG. 4, actuation system according to embodiments of the present invention can have any suitable number of pressure sensors in any suitable arrangement. As previously discussed with respect to FIGS. 1A ands 1B, the inclusion of pressure sensors in actuation system 100 serves to enable the determination of the force with which detector cap 102 is urged against a target site.

Figure 5:
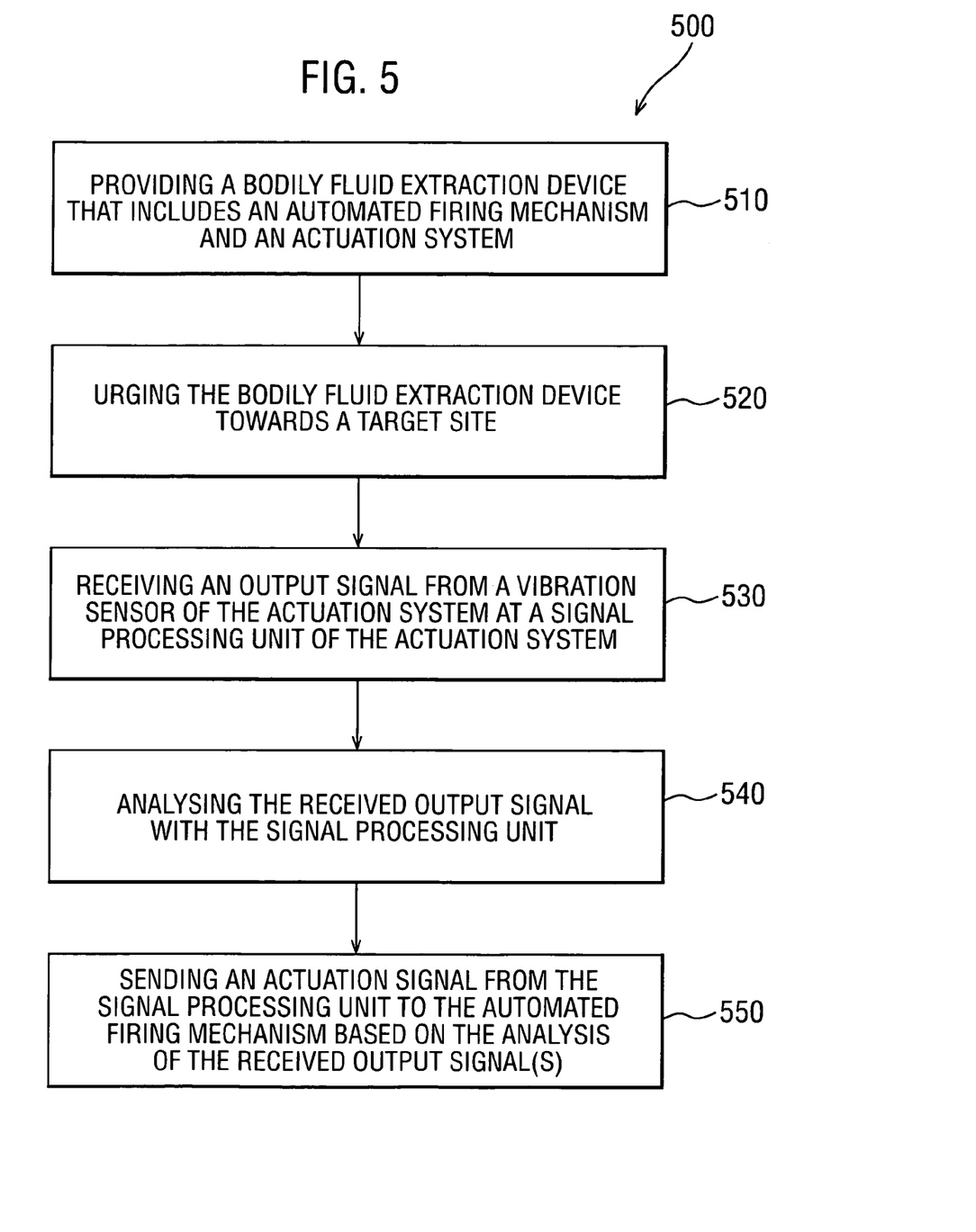
FIG. 5 is a flow chart illustrating a sequence of steps in a process according to an exemplary embodiment of the present invention.

FIG. 5 is a flow chart depicting a sequence of steps in a method for extracting a bodily fluid sample 500 according to an exemplary embodiment of the present invention. Method 500 includes providing a bodily fluid extraction device that includes an automated firing mechanism and an actuation system, as set forth in step 510. The actuation system of the bodily fluid extraction device includes a detector cap, at least one vibration sensor(s) connected to the detector cap and at least one signal processing unit(s) in communication with the vibration sensor(s). In addition, the signal processing unit is configured to receive an output signal from each of the vibration sensors, to analyze the received output signal, and to send an actuation signal to the automated firing mechanism based on the analysis of the received output signal.

Optionally, the actuation system of the bodily fluid extraction device can include at least one pressure sensor(s) with the signal processing unit being configured to receive a signal from the pressure sensor(s), to analyze the received signal from the pressure sensor, and to send an actuation signal to the automated firing mechanism based on the analysis of both the received signal from the pressure sensor and the output signal from the vibration sensor.

The bodily fluid extraction device provided in step 510 can be, for example, bodily fluid extraction device 300 of FIG. 3, bodily fluid extraction device 400 of FIG. 4, or any other bodily fluid extraction device according to embodiments of the present invention.

Next, the bodily fluid extraction device is urged towards a target site (for example, a dermal tissue target site of a user's finger), as set forth in step 520 of FIG. 5. Subsequently, an output signal from the vibration sensor(s) is received by the signal processing unit, as set forth in step 530.

The signal processing unit is then employed to analyze the received output signal (see step 540). This analysis can include analyses of the received signals as have been previously described with respect to the actuation system of FIGS. 1A and 1B and the bodily fluid extraction device of FIG. 3. Thereafter, an actuation signal is sent to the automated firing mechanism from the signal processing unit based on the analysis of the received output signal, as set forth in step 550.

In the circumstance that the actuation system optionally includes pressure sensors, step 540 further includes the receiving of a signal from each of the pressure sensor(s) by the signal processing unit. In addition, step 550 includes employing the signal processing unit to analyse the signal received from the pressure sensor, and step 560 includes sending an actuation signal to the automated firing mechanism from the signal processing unit based on the analyses of the received output signal from the vibration sensor and the received signal from the pressure sensor.

Since methods according to the present invention include sending an actuation signal from the signal processing unit based on an analysis of received output signals from vibration sensors, a user can not readily anticipate when such actuation will occur and does not have to manually actuate the bodily fluid extraction device. Therefore, user pain and/or discomfort associated with such anticipation and manual activation are eliminated.

It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for actuating a bodily fluid extraction device, the method comprising:
   providing a bodily fluid extraction device that includes an automated firing mechanism and an actuation system, the actuation system having:
      a detector cap with a proximal surface;
      at least one vibration sensor connected to the detector cap; and
      a signal processing unit in communication with each of the at least one vibration sensor,
         wherein the signal processing unit is configured to receive an output signal from each of the at least one vibration sensor, to analyse the received output signal, and to send an actuation signal to the automated firing mechanism device based on the analysis of the received output signal.
   urging the bodily fluid extraction device towards a target site;
   receiving an output signal from each of the at least one vibration sensor by the signal processing unit;
   employing the signal processing unit to analyse the output signal received from each of the at least one vibration sensor;
   sending an actuation signal to the automated firing mechanism from the signal processing unit based on the analysis.

2. The method of claim 1, wherein sending step includes sending an actuation signal when the analysis indicates that the detector cap is symmetrically urged against the target site.

3. The method of claim 1, wherein the providing step includes providing a bodily fluid extraction device that includes an actuation system with at least one pressure sensor; and     the receiving step includes the receiving of a signal from each of the at least one pressure sensor at the signal processing unit; and     the employing step includes employing the signal processing unit to analyse the signal received from each of the at least one pressure sensor; and     the sending step includes sending an actuation signal to the automated firing mechanism from the signal processing unit based on the analysis of the received output signal from each of the at least one vibration sensor and the received output signal from each of the at least one pressure sensor.

\* \* \* \* \*